United States Patent [19]

Wristers

[11] 4,085,035
[45] Apr. 18, 1978

[54] HYDROGENATION PROCESS USING NOBLE METAL CATALYSTS PROMOTED BY LIQUID FLUORINE CONTAINING ACIDS

[75] Inventor: Jos Wristers, Baton Rouge, La.

[73] Assignee: Exxon Research & Engineering Co., Linden, N.J.

[21] Appl. No.: 748,209

[22] Filed: Dec. 7, 1976

Related U.S. Application Data

[63] Continuation-in-part of Ser. No. 577,351, May 14, 1975, Pat. No. 4,025,459.

[51] Int. Cl.$^2$ .................. C07C 5/10; C10G 23/04
[52] U.S. Cl. ..................................... 208/143; 260/667
[58] Field of Search ......................... 208/143; 260/667

[56] References Cited

U.S. PATENT DOCUMENTS

| 3,409,684 | 11/1968 | Aristoff et al. | 260/677 |
| 3,888,937 | 6/1975 | Siskin et al. | 260/677 |

Primary Examiner—Herbert Levine
Attorney, Agent, or Firm—Joseph J. Allocca

[57] ABSTRACT

A process for the hydrogenation of unsaturated hydrocarbon fractions is described which comprises dissolving said unsaturated hydrocarbon fraction in a liquid acid system, said liquid acid system being selected from the group consisting of liquid HF, other liquid Bronsted acid containing fluorine, fluorine containing Friedel-Crafts catalyst (such as BF$_3$, TaF$_5$) in liquid HF or other liquid fluorine containing Bronsted acid and contacting the resulting solution with a catalyst selected from the group consisting of the elemental oxide and sulfide forms of platinum and iridium and the elemental and oxide forms of palladium promoted with a liquid acid system said liquid acid system being selected from the group consisting of liquid fluorine containing Bronsted acid and fluorine containing Friedel-Crafts catalyst in liquid fluorine containing Bronsted acid in a pressurized hydrogen atmosphere at a temperature sufficient to facilitate the reaction and avoid hydrocracking.

Hydrogenation using a liquid fluorine containing Bronsted acid promoted palladium system as catalyst has been found to be from 10 to 144 times more active than palladium by itself. Hydrogenation using palladium promoted by using a Friedel-Crafts catalyst containing fluorine in conjunction with a liquid fluorine containing Bronsted acid demonstrates an activity increase on the order of 3500 times. Using platinum or iridium promoted as described above results in a hydrogenation process which is tolerant to sulfur and therefore one highly attractive when dealing with heavy ends, resid, coal liquids or other high sulfur, difficult to process hydrocarbon feedstreams.

In the practice of the instant process, the liquid acid promoted platinum, palladium and iridium catalyst material may be supported on any material resistant to acid, carbon, charcoal, Teflon, (polytetrafluoroethylene) etc., meeting this requirement.

30 Claims, No Drawings

HYDROGENATION PROCESS USING NOBLE METAL CATALYSTS PROMOTED BY LIQUID FLUORINE CONTAINING ACIDS

CROSS-REFERENCE TO RELATED APPLICATIONS

This application is a continuation-in-part of Ser. No. 577,351 filed May 14, 1975, now U.S. Pat. No. 4,025,459.

DESCRIPTION OF THE INVENTION

A process for the hydrogenation of unsaturated hydrocarbon fractions is described which comprises dissolving said unsaturated hydrocarbon fraction in a liquid acid system, said liquid acid system being selected from the group consisting of liquid HF, other liquid Bronsted acid containing fluorine, fluorine containing Friedel-Crafts catalyst (such as $BF_3$, $TaF_5$, etc.) in liquid HF or other liquid fluorine containing Bronsted acid and contacting the resulting solution with a catalyst selected from the group consisting of the elemental, oxide and sulfide forms of platinum and iridium and the elemental and oxide forms of palladium promoted with a liquid acid system, said liquid acid system being selected from the group consisting of liquid fluorine containing Bronsted acid and fluorine-containing Friedel-Crafts catalyst in liquid Bronsted acid containing fluorine in a pressurized hydrogen atmosphere at a temperature sufficient to facilitate the hydrogenation reaction and avoid hydrocracking.

Adding liquid HF or liquid Bronsted acids containing fluorine to palladium results in a catalyst demonstrating enhanced hydrogenation activity on the order of 10 to 144 times that of palladium by itself. Adding a Friedel-Crafts catalyst containing fluorine, e.g., boron fluoride, tantalum fluoride, niobium fluoride and mixtures thereof, to the liquid HF or liquid Bronsted acid-containing fluorine leads to even greater hydrogenation rate increases, e.g., 3500 times. Alternatively, addition of liquid HF or a fluoride-containing Friedel-Crafts catalyst in liquid HF or Bronsted acid containing fluorine to platinum also results in enhanced hydrogenation rates but to a lesser degree than with palladium. However, such liquid acid promoted platinum catalysts are more tolerant to sulfur, than are palladium catalysts making them attractive as a heavy ends, resid and coal liquid hydrogenation catalyst. Iridium has also been discovered to be a good hydrogenation catalyst when used in the presence of liquid HF or fluorine containing Bronsted acid or fluorine containing Friedel-Crafts catalysts in liquid HF or Bronsted acid containing fluorine. Hydrogenation is increased approximately 150 fold. Such liquid acid promoted iridium catalysts are more tolerant to sulfur, than are palladium catalysts making them attractive as heavy end, resid and coal liquid hydrogenation catalysts.

The liquid acid promoted palladium, platinum or iridium catalyst may be supported on a material resistant to acid. The support material may be any common material; carbon, charcoal, Teflon (polytetrafluoroethylene), etc., meet this requirement.

The palladium may be in the elemental or oxide form (as described above), the elemental form being preferred while the platinum and iridium may be in the elemental, oxide or sulfide forms (as described above) the elemental forms again being preferred. The instant process is especially useful for the hydrogenation of heavy ends, resid and coal liquids. The unsaturated hydrocarbon fractions typically comprise aromatic, heterocyclic aromatic, condensed polynuclear aromatic and condensed polynuclear heterocyclic aromatic compounds ranging from $C_6$ to polymeric and the heteroatom is sulfur or nitrogen.

PRIOR ART

The processing of heavy hydrocarbon fractions such as residua, viscous crudes, tars, shale oils and the like is particularly difficult since these fractions contain considerable quantities of both mononuclear and polynuclear aromatic hydrocarbon and heterocyclic aromatic compounds and particularly condensed polynuclear aromatic hydrocarbon compounds and condensed polynuclear heterocyclic aromatic compounds. When these condensed ring compounds are subjected to catalytic cracking, they produce large amounts of coke and gas with only a minor yield of useful liquid product as compared to the yield of liquid product obtained from conventional distillate cracking stocks. Furthermore, these compounds have a high viscosity and in the case of the heterocyclic compounds they have a tendency to form chelate structures with metals. These chelated compounds, when cracked, deposit the metals on the cracking catalyst, which in turn adversely affects the cracking characteristics of the catalyst with respect to product distribution.

A method to circumvent these processing problems has been to hydrogenate the unsaturated compound prior to cracking. It is to be expected that such hydrogenation would result in compounds which can be catalytically cracked more selectively with the production of less coke and a higher yield of useful liquid products. Such hydrogenated products would have lower viscosity and therefore could be more readily handled at lower temperatures and such hydrogenation would reduce the amount of chelated metal present in the cat cracking feedstream thereby avoiding to a great extent catalyst fouling.

Typically, the aromatic hydrocarbons of interest have been reduced at high temperatures, using nickel or other metals as a catalyst in the presence of high hydrogen pressures.

R. Adams and J. R. Marshall in "The Use of Platinum Oxide Platinum Black in the Catalytic Reduction of Aromatic Hydrocarbons," J. Am. Chem. Soc. 50 1970 (1928) revealed the usefulness of noble metal in the catalytic hydrogenation of unsaturated hydrocarbon. Their work was directed to improving the activity of the catalyst. The reaction was carried out with glacial acetic acid as the preferred solvent.

J. H. Broun, H. W. Durand and C. S. Marvel in J. Am. Chem. Soc. 58 (1594) (1936) teach "The Reduction of Aromatic Compounds with Hydrogen and a Platinum Oxide-Platinum Black Catalyst in the Presence of Halogen Acid." The halogen acids used in every experiment were HCl or HBr. It was noted that addition of such acid increased the effectiveness of the platinum oxide-platinum black catalyst.

T. Baker and R. Schuetz in J. Am. Chem. Soc. 69 (1250) 1946 disclosed "High Pressure Hydrogenations with Adams Catalyst." This work extended the usefulness of the original platinum oxide-platinum black catalyst by the expedient of increased hydrogen pressure. All other parameters, such as temperature and solvent (in this case, acetic acid) remained constant.

British Pat. No. 1,104,409 to Shell, teaches an improved process for the "Hydrocracking of Hydrocarbon Oils" which utilizes a tungsten-nickel catalyst on alumina which alumina has a small wt. % of silica and at least 3.5 wt. % fluorine. It must be noted that this invention is directed to a cracking process and not to hydrogenation.

U.S. Pat. No. 3,435,085 to White and Houston, teaches "Aromatic Hydrogenation using a Fluorided Alumina Catalyst." This process hydrogenates aromatics in the presence of sulfur over a nonsiliceous catalyst containing a Group VIII hydrogenation metal disposed on an essentially nonsiliceous support comprising alumina and 10–35% fluorine measured as the element. Platinum is the preferred metal. The patent teaches a reaction run at 650°–900° F. (340°–480° C.) at a pressure above 500 psia, preferably 1000–4000 psia. The support taught is alumina, the fluorine being added to the catalyst before or after deposition of the metal. The addition of fluorine causes a stoichiometric conversion of alumina to aluminum fluoride, that is, the fluorine reacts with the support. Furthermore, the reaction is run without the addition of excess HF. Gaseous or liquid HF or fluorine compounds are used only to initally activate and periodically reactivate the alumina supported catalysts unlike the instant invention which utilizes liquid HF or Bronsted acid containing fluorine or liquid Friedel-Crafts metal fluoride in HF or Bronsted acid containing fluorine system as an actual reactive phase of the process.

U.S. Pat. No. 3,409,684 to Aristoff et al teaches a process for the partial hydrogenation of aromatic compounds which consists of contacting the compound with hydrogen at elevated temperatures and pressures in the presence of a catalyst consisting of a metal hydrogenation component and a Friedel-Crafts metal halide gaseous hydrogen halide component. This patent teaches the necessity of there being a mixture of Friedel-Crafts metal halide and hydrogen halide in combination with the catalytic metal if appreciable hydrogenation rates and yields are to be obtained. The patent, however, utilizes gaseous hydrogen halide and Friedel-Crafts metal catalyst. The patent broadly discloses palladium on activated carbon with Friedel-Crafts metal halide and gaseous hydrogen halide in the body of the specification and then proceeds by Table IV to demonstrate that such a system, when the halogen is fluorine, is inefficient and undesirable; that to get any appreciable reaction, it is necessary to use both Friedel-Crafts type metal halide and hydrogen halide in combination with the catalytic metal, and in order for there to be a reasonable degree of hydrogenation, temperatures over 100° C and pressures exceeding 500 psi and up to 2000 psi are required. This patent in its enumeration of Friedel-Crafts metal halide also does not disclose tantalum pentafluoride or Ir on carbon. The claims of the case are directed only to aluminum chloride-gaseous hydrogen chloride catalyst systems.

The instant invention teaches the unexpected discovery that the addition of liquid HF, Bronsted acid containing fluorine or Friedel-Crafts type metal fluoride catalyst (e.g., boron fluoride, tantalum fluoride, niobium fluoride and mixtures thereof) in liquid HF or Bronsted acid containing fluorine to palladium, produces a catalyst which demonstrates enhanced hydrogenation activity on the order of 14 to 3600 times that of the palladium by itself and this activity enhancement is achieved at low temperature and moderate hydrogen pressures, the temperature ranging from 20° to 200° C, preferably 25°–60° C, most preferably 40° C. Hydrogen pressures on the order of 25 to 5000 psig, preferably 50–1000 psig and most preferably, 100–500 psig, were found to work satisfactorily. The palladium may be deposited on a nonacidic acid resistant support material such as carbon, charcoal, Teflon (polytetrafluoroethylene), etc. Reaction times can be from 1 minute to 12 hours, preferably 1 minute to 5 hours, most preferably, 1 minute to 1 hour depending on feed composition and chosen reaction temperature and pressure.

The liquid Bronsted acids containing fluorine may be selected from the group comprising HF, fluorosulfonic acid, trifluoromethane sulfonic acid. The preferred acid is liquid hydrogen fluoride.

The materials which are envisioned as suitable feeds for use with the instant catalyst to yield hydrogenation product comprises unsaturated hydrocarbon fractions, which fractions are aromatic, condensed polynuclear aromatic and condensed polynuclear heterocyclic aromatics ranging from $C_6$ to polymeric typically $C_6$ to $C_{800}$ unsaturated materials and wherein the hetero atoms are sulfur and nitrogen.

It has also been discovered that addition of the Friedel-Crafts metal catalyst $TaF_5$, substantially enhances the rate of reaction selectivity to desired products and yields at temperatures up to 50° C. and hydrogen pressures of about 400 psig. Temperatures above 50° C. are to be avoided as above 50° C hydrocracking occurs with $TaF_5$ seriously interfering with the desired hydrogenation. Preferably, the reaction temperature is 40° C.

With other fluoride containing Friedel-Crafts catalysts in hydrogen fluoride, it has been discovered that the prior art teaching of the necessity of there being high temperatures and/or high hydrogen pressures is applicable only to gaseous acid systems, a rate increase by contrast of over 3600 being observed with liquid systems at 30° C and 400 psig (see Run 4, Table I) in the instant invention.

Addition of liquid HF or liquid acids containing fluorine to platinum or iridium also produces a catalyst with improved hydrogenation activity and superior sulfur resistance. These catalytic materials in elemental, oxide or sulfide form may be supported on a nonacidic acid resistant support material, any typical material being satisfactory; carbon, charcoal, teflon (polytetrafluoroethylene), etc., are satisfactory. The support of choice is carbon.

The catalysts of this invention comprise 0.01 to 10% Pd, Pt or Ir, preferably 1–7%, most preferably, 5% Pd, Pt or Ir. These percentages refer to the percent of noble metal on a support. The palladium may be in oxide or in elemental metal form, elemental metal being preferred, while the Pt or Ir may be in elemental, oxide or sulfide form. These catalyst materials may be supported on a nonacidic acid resistant carrier, such as carbon, charcoal, teflon (Polytetrafluoroethylene), etc. This catalyst is then promoted with a liquid acid system selected from the group consisting of liquid HF acid, Bronsted acid containing fluorine or Friedel-Crafts metal fluoride in liquid HF or Bronsted acid containing fluorine. If no support is used and the metals in their elemental, oxide, or sulfide form are dispersed in the liquid acid, the percentage of noble metal based on the total acid weight should be in the range of 0.0001%–10%, preferably 0.01–1% and most preferably 0.1% . The reaction is run in the presence of the liquid acid system as a reaction media component.

Catalysts of the above composition demonstrate synergistic rate, yield and selectivity enhancements as compared to metal catalysts or acid catalysts alone and produce the superior result at lower temperatures and pressures than the prior art, temperatures of choice being between 20°–200° C., preferably 25°–60° C, most preferably, 40° C. Hydrogen pressures range from 25–5000 psig, preferably 50–1000 psig, most preferably 100–500 psig.

The following examples will demonstrate the superiority of the instant invention but are not to be construed as limitations on the scope or breadth of the invention, various modifications being within the ability of those skilled in the art and clearly within the realm of the invention.

The amount of Friedel-Crafts metal fluoride which is added to the liquid HF or Bronsted acid containing fluorine is entirely within the discretion of the practitioner, a ratio of from 1:1000 to 1:1 Friedel-Crafts metal fluoride:Bronsted acid containing fluorine being entirely consistent with the object and operability of the instant invention.

The instant invention also constitutes a process for hydrogenating homocyclic and heterocyclic, mononuclear and polynuclear aromatic compounds which utilizes the catalyst as described above. When these aromatic compounds dissolved in alkane solvents are brought in contact with the catalyst of the instant invention, the aromatic compound is abstracted into the liquid acid phase. The saturated paraffin solvent is insoluble in the liquid acid phase. The aromatic compound dissolved in the acid is protonated to the carbonium ion species and this species contacts the metal catalyst, at which time the aromatic material became hydrogenated and being insoluble with acid, migrates to the paraffin phase. Additional aromatic material in the paraffin solvent can, consequently, dissolve in the acid phase thereby constituting a continuous separation.

EXAMPLE 1

A number of experiments were run to determine the effect of using different acids in conjunction with different noble metals as catalysts for the hydrogenation 0.100 moles of mesitylene, Table I.

The experimental procedure followed is described for run number 5. A similar procedure was followed for all the runs described in this example and the following examples. To a 300 cc Hasteloy-C autoclave was added 1.0 g 5% Pd/C, 12.0 g (0.100 mole) mesitylene, 55.2 g (0.200 mole) tantalum pentafluoride, and 46.0 g (2.3 moles) of hydrogen fluoride. The autoclave was stirred, heated to 30° C, and pressured with 400 psig hydrogen. As hydrogen was consumed the pressure dropped. When the pressure dropped to 360 psig, hydrogen was added to bring the pressure back to 400 psig. This procedure was repeated until no more hydrogen was consumed. The total product was added to ice, heated to room temperature and extracted with ether. The combined ether extracts were washed with aqueous sodium bicarbonate, and then water. They were dried and the solvent was removed at reduced pressure. The yield was 8.4 g, 70%. The product was then analyzed by a combination of mass spectroscopy, nuclear magnetic resonance and gas chromatography. This analysis indicated that approximately 94% of the material was trimethylcyclohexane or isomers thereof. The other 6% product was mesitylene that had been clogged in a dipleg and thus never come in contact with the catalyst.

On the basis of the product analysis and the hydrogen consumption one could calculate when one half of the mesitylene was hydrogenated. This point was designated $t_{\frac{1}{2}}$. This $t_{\frac{1}{2}}$ was divided into the $t_{\frac{1}{2}}$ that was obtained for the similar reaction run at the same temperature and hydrogen pressure but in the absence of any acid. This produced the rate increase for the acid catalyzed reaction. Thus, the rate increase for run 5 is obtained by dividing the $t_{\frac{1}{2}}$ of run 2 by that of run 5; the rate increase of run 7 is obtained by dividing the $t_{\frac{1}{2}}$ of run 1 by that of run 7; and the rate increase of run 9 is obtained by dividing the $t_{\frac{1}{2}}$ of run 8 by that of run 9, etc.

TABLE I

| Run | Acid, moles | Metal 5 %/C, g | Temp. °C | $t_{\frac{1}{2}}$ Minutes | Rate Increase $t_{\frac{1}{2}}$ No Acid ÷ $t_{\frac{1}{2}}$ Acid Catalyzed |
|---|---|---|---|---|---|
| 1* | None | Pd/C, 1.0 | 50 | 5,458 | — |
| 2* | None | Pd/C, 1.0 | 30 | 12,717** | — |
| 3 | HF, 2.2 - liquid | Pd/C, 1.0 | 30 | 88 | 144 |
| 4 | HF/BF$_3$, 2.3/0.23 | Pd/C, 1.0 | 30 | 3.5 | 3630 |
| 5 | HF/TaF$_5$, 2.3/0.20 | Pd/C, 1.0 | 30 | 5.0 | 2540 |
| 6 | TaF$_5$, 0.20 | Pd/C, 1.0 | 30 | - | 0 |
| 7* | HF, 0.075 - gas | Pd/C, 1.0 | 50 | 90 | 61 |
| 8* | None | Ir/C, 1.8 | 30 | 1,300 | — |
| 9 | HF/TaF$_5$, 2.2/0.20 | Ir/C, 1.8 | 30 | 8.5 | 153 |
| 10* | None | Pt/C, 1.83 | 30 | 299 | — |
| 11 | HF/TaF$_5$, 2.4/0.20 | Pt/C, 1.83 | 30 | 22 | 14 |
| 12 | None | Ru/C, 5.0 | 30 | 8.5 | — |
| 13 | HF/TaF$_5$, 2.36/0.20 | Ru/C, 5.0 | 30 | 17,372 | 0.0005 |
| 14 | None | Rh/C, 5.10 | 37 | 2.3 | — |
| 15 | HF/TaF$_5$, 2.21/0.20 | Rh/C, 5.10 | 30 | 26 | 0.09 |
| 16 | HCl, 1.38 | Pd/C, 1.0 | 30 | — | 0 |
| 17 | HCl/AlCl$_3$, 1.03/0.10 | Pd/C, 1.0 | 30 | — | 0 |
| 18 | HBr/AlBr$_3$, 0.97/0.10 | Pd/C, 1.0 | 30 | — | 0 |
| 19 | HCl, 1.09 | Pt/C, 1.0 | 30 | 84 | 3.6 |
| 20 | HCl/AlCl$_3$, 0.92/0.100 | Pt/C, 1.0 | 30 | 324 | 0.92 |

* Used 103 ml of pentane as the solvent.
** estimated

These runs demonstrate the following:

Run 3 demonstrates that liquid HF catalyzes the hydrogenation ability of palladium on carbon.

Runs 4 and 5 demonstrate that adding a Friedel-Crafts catalyst to liquid HF increases the hydrogenation ability of the acid even more.

Run 6 demonstrates that a Friedel-Crafts alone does not catalyze the hydrogenation of palladium on carbon.

Run 7 demonstrates that only gaseous amounts of HF need to be present in order for rate enhancements to be observed.

Runs 9 and 11 demonstrate that HF acids catalyze the hydrogenation ability of iridium on carbon and also of platinum on carbon.

Runs 13 and 15 demonstrate that HF acids do not catalyze the hydrogenation ability of noble metals besides Pd, Pt and Ir. In fact they inhibit the hydrogenation ability of Ru and Rh.

Runs 16, 17 and 18 demonstrate that acids other than ones containing HF do not catalyze the hydrogenation ability of palladium. In fact HCl, HCl/AlCl$_3$ and HBr/AlBr$_3$ completely deactivate the hydrogenation ability of Pd/C.

Runs 19 and 20 demonstrate that acids other than ones containing HF do not have much effect on the hydrogenation ability of platinum. Analyses of the products on run 19 indicated that some products were formed that were not formed in any of the other experiments. These products were either isomers of completely hydrogenated mesitylene or chlorinated trimethylcyclohexane.

EXAMPLE 2

A number of experiments were run to establish that the HF catalyzed palladium on carbon hydrogenation was a general reaction in terms of aromatic feeds. In each run 0.10 mole of the aromatic, the acid, and 5% palladium on carbon were charged. All reactions were run at 30° C. In runs 24 through 27, 103 ml of pentane was used as a solvent. The experimental procedure, hydrogen pressure, and work-up was the same as in Example 1.

TABLE II

| Run | Aromatic | Acid, Moles | $t_{\frac{1}{2}}$ Minutes | Rate, Increase $t_{\frac{1}{2}}$ No Acid ÷ $t_{\frac{1}{2}}$ Acid Catalyzed |
|---|---|---|---|---|
| 21* |  | — | 4,500 | — |
| 22 |  | HF, 2.4 | 182 | 25 |
| 23 |  | HF/TaF$_5$, 2.4/0.20 | 26 | 173 |
| 24 | 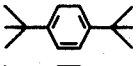 | — | 3,251 | — |
| 25 |  | HF, 0.045 | 185 | 18 |
| 26 | 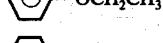 | — | 1,620 | — |
| 27 | 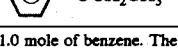 | HF, 0.05 | 175 | 9 |

*Used 1.0 mole of benzene. The $t_{\frac{1}{2}}$ was based on hydrogenating 0.05 moles of the benzene.

Runs 21 through 27 demonstrate that adding HF acids to palladium increases its hydrogenation activity. The acid can be liquid HF (run 22) liquid HF/TaF$_5$ (run 23), or gaseous HF (run 25 or 27). The aromatic can also contain functional groups such as oxygen (run 27).

EXAMPLE 3

One experiment was run to demonstrate the applicability of using an HF promoted palladium on carbon catalyst to hydrogenate a C$_{14}$–C$_{17}$ commercial solvent distillate. The C$_{14}$–C$_{17}$ paraffinic solvent contains about 5% aromatics. The saleable solvent must have less than 1% aromatic. This level is accomplished by hydrogenating the aromatics. Two experiments were run in a 300 cc Hasteloy-C autoclave. One utilized an HF-Pd/C hydrogenating catalyst and the other only Pd/C. Both utilized 100 ml of distillate and were run at 150° C. The initial hydrogen pressure was 350 psig. The rate and the quantity of hydrogen that was consumed was used to measure the progress of the reaction. The reaction was run until no further hydrogen was consumed.

TABLE III

| Run | Acid, Moles | Total Hydrogen Consumption, PSIG | $t_{\frac{1}{2}}$, time to reach One-Half of H$_2$ Consumption Minutes | Rate Increase $t_{\frac{1}{2}}$ run 28 ÷ $t_{\frac{1}{2}}$ run #29 |
|---|---|---|---|---|
| 28 | | 137 | 50 | |
| 29 | HF, 0.18 | 159 | 20 | 2.5 |

Run 29 demonstrates that adding HF to Pd/C leads to a 250% rate increase in hydrogenating C$_{14}$–C$_{17}$ distillate. The resultant product contains less than 0.5% aromatics and thus surpasses the required product specifications. The total hydrogen consumption in the HF-Pd/C reaction is also greater than in the Pd/C, reaction (159 vs 139 psig H$_2$) thus indicating that the extent of hydrogenation in the acid catalyzed reaction is more complete.

EXAMPLE 4

A number of experiments were carried out to differentiate the liquid acid-Pd/C hydrogenation catalyst from the gaseous acid-Pd/C hydrogenations disclosed in U.S. Pat. No. 3,409,684. Anthracene was used in these studies. The results obtained with anthracene are analogous to the results obtained in model systems involving pyrene. All the equipment, procedure and work-up are the same as described in the previous example. Table IV presents the results.

TABLE IV

| Experiment | 30 4293-32 | 31 3540-20 | 32 4026-129 | 33 2907-69 |
|---|---|---|---|---|
| HF, mole | — | 0.20 | 2.3 | 2.3 |
| TaF$_5$, mole | — | — | 0.20 | 0.20 |
| Pd/C 5%, g. | 1.0 | 1.0 | 1.0 | — |
| Pentane, mole | 0.9 | 0.9 | — | — |
| Hydrogen Press. Range, psig | 1000 | 900–1000 | 400–500 | 810–815 |
| Temperature, ° C. | 100 | 100 | 70 | 80 |
| Time, hrs. | 4 | 3 | 6.5 | 19.5 |
| Hydrogen Press. Consumption, psig | 70 | 310 | 1464 | 0 |
| Products and Recovered Anthracene | | | | |
| Anthracene | 32% | 0% | traces | 100% |
| Partially hydrogenated Anthracene | 68% | 100% | 0% | 0% |
| Completely hydrogenated Anthracene | 0% | traces | 27% | 0% |
| Hydrocracked Products | 0% | 0% | 73% | 0% |

Run 30 indicates that in the absence of any acid Pd/C has little hydrogenation ability at these mild conditions only 70 psig of hydrogen is consumed and no completely hydrogenated anthracenes are formed.

Run 31 indicates that the addition of small amounts of HF catalyzes the hydrogenation activity of Pd/C. 310 psig of hydrogen were consumed as opposed to almost no hydrogen in the preceding run done in the absence of any acid. Only partially hydrogenated anthracenes, but no completely hydrogenated anthracenes were formed.

Run 32 indicates that liquid HF/TaF$_5$ catalyzes the hydrogen of Pd/C much more so than gaseous HF. The hydrogen uptake is 1464 psig as opposed to 310 psig in the gaseous HF experiment. Note also that the temperature is 30° C. less than in the liquid acid experiment so one would expect much less hydrogen consumption. Only completely hydrogenated anthracenes are formed in this system. Some of these completely hydrogenated anthracenes are hydrocracked by the acid at these high temperatures. However, at lower temperatures they can all be easily separated with minimal hydrocracking.

Run 33 indicates that in the absence of Pd/C, liquid HF/TaF$_5$ has no hydrogenating ability.

What is claimed is:

1. A process for the hydrogenation of aromatic compounds in an unsaturated hydrocarbon fraction comprising them which comprises contacting said unsaturated hydrocarbon fraction with a catalyst selected from the group consisting of the elemental, oxide and sulfide forms of platinum and iridium and the elemental and oxide forms of palladium promoted with a liquid acid system, said liquid acid system being selected from the group consisting of liquid Bronsted acids containing fluorine and fluorine containing Friedel-Crafts catalyst in liquid Bronsted acids containing fluorine, said contacing being conducted in the presence of said liquid acid system in a pressurized hydrogen atmosphere at a temperature sufficient to facilitate the reaction.

2. The process of claim 1 wherein the unsaturated hydrocarbon fraction comprises mononuclear aromatic hydrocarbons, heterocyclic aromatic hydrocarbons, condensed polynuclear aromatic hydrocarbons and condensed polynuclear heterocyclic aromatic hydrocarbons.

3. The process of claim 1 wherein the unsaturated hydrocarbon fraction comprises a C$_6$ to polymeric aromatic compound.

4. The process of claim 1 wherein the unsaturated hydrocarbon fraction comprises a heterocyclic aromatic hydrocarbon of from C$_6$ to polymeric and the hetero atoms are sulfur and nitrogen.

5. The process of claim 1 wherein the unsaturated hydrocarbon fraction comprises a C$_6$ to C$_{800}$ aromatic compound.

6. The process of claim 5 wherein said hydrogenation is carried out at a hydrogen pressure of from 25 to 5000 psig.

7. The process of claim 6 wherein said hydrogenation is carried out at a hydrogen pressure between 100 to 1000 psig.

8. The process of claim 7 wherein the hydrogenation pressure is 100 to 500 psig.

9. The process of claim 8 wherein the temperature of the reaction is between 20° to 200° C.

10. The process of claim 9 wherein the temperature of the reaction is between 25° to 60° C.

11. The process of claim 1 wherein said elemental, oxide and sulfide form of platinum and iridium and elemental and oxide form of palladium are supported on a nonacidic acid resistant support.

12. The process of claim 11 wherein said nonacidic acid resistant support is selected from the group consisting of carbon, charcoal and polytetrafluoroethylene.

13. The process of claim 1 wherein said liquid Bronsted acid containing fluorine is selected from the group consisting of fluoro-sulfonic acid, trifluoromethanesulfonic acid and hydrogen fluoride.

14. The process of claim 1 wherein said liquid acid system is a fluorine containing Friedel-Crafts catalyst in liquid Bronsted acid containing fluorine.

15. The process of claim 1 wherein said fluorine containing Friedel-Crafts catalyst is selected from the group consisting of boron fluorides, tantalum fluorides and niobium fluorides.

16. The process of claim 1 wherein said fluorine containing Friedel-Crafts catalyst is selected from the group consisting of BF$_3$ and TaF$_5$.

17. The process of claim 1 wherein the platinum, palladium and iridium are in the elemental form.

18. A process for the hydrogenation of aromatic compounds in an unsaturated hydrocarbon fraction comprising them which comprises contacting said fraction with elemental Pd on carbon promoted with BF$_3$ in liquid HF at between 25 to 500 psig hydrogen pressure at a temperature of from 25° to 50° C.

19. A process for the hydrogenation of aromatic compounds in heavy hydrocarbon feeds containing sulfur which comprises contacting said sulfur-containing feed with a catalyst selected from the group consisting of the elemental, oxide and sulfide forms of platinum and iridium promoted with a liquid acid system, said liquid acid system being selected from the group consisting of liquid Bronsted acids containing fluorine and fluorine containing Friedel-Crafts catalyst in liquid Bronsted acids containing fluorine, said contacting being conducted in the presence of said liquid acid system in a pressurized hydrogen atmosphere at a temperature sufficient to facilitate the reaction.

20. The process of claim 19 wherein said hydrogenation is carried out at a hydrogen pressure of from 25 to 5000 psig.

21. The process of claim 20 wherein the hydrogen pressure is between 100 to 500 psig.

22. The process of claim 21 wherein the temperature is between 20° to 200° C.

23. The process of claim 22 wherein the temperature is between 25° to 60° C.

24. The process of claim 19 wherein said elemental, oxide and sulfide forms of platinum and iridium are supported on a nonacidic, acid resistant support.

25. The process of claim 19 wherein the platinum and iridium are in the elemental form.

26. A process for the hydrogenation of aromatic compounds in heavy hydrocarbon feeds containing sulfur which comprises contacting said feeds with platinum or idirium on carbon promoted with BF$_3$ in liquid HF, said contacting being carried out in a hydrogen atmosphere of from 25 to 500 psig at a temperature of from 25° to 60° C,.

27. The process of claim 18 wherein the temperature is 30° C.

28. The process of claim 1 wherein the fluorine containing Friedel-Crafts catalyst is TaF$_5$, the catalyst is elemental platinum supported on carbon and the Bronsted acid is HF.

29. The process of claim 26 wherein the temperature is 40° C.

30. The process of claim 19 wherein the catalyst is elemental platinum, the fluorine containing Friedel-Crafts catalyst is TaF$_5$ and the Bronsted acid is HF.

* * * * *